(12) United States Patent
Ohnishi et al.

(10) Patent No.: US 8,691,559 B2
(45) Date of Patent: Apr. 8, 2014

(54) MICRO CHANNEL, DEVICE FOR RECOVERING NUCLEIC ACID AND METHOD FOR RECOVERING NUCLEIC ACID

(75) Inventors: Michihiro Ohnishi, Kanagawa (JP); Yuta Kan, Tokyo (JP); Tomoteru Abe, Kanagawa (JP)

(73) Assignee: Sony Corporation, Tokyo (JP)

(*) Notice: Subject to any disclaimer, the term of this patent is extended or adjusted under 35 U.S.C. 154(b) by 1697 days.

(21) Appl. No.: 11/858,595

(22) Filed: Sep. 20, 2007

(65) Prior Publication Data

US 2008/0161553 A1 Jul. 3, 2008

(30) Foreign Application Priority Data

Sep. 22, 2006 (JP) ................ P2006-257791

(51) Int. Cl.
| | | |
|---|---|---|
| C12M 1/34 | (2006.01) | |
| C12M 3/00 | (2006.01) | |
| C12Q 1/68 | (2006.01) | |
| B01D 15/08 | (2006.01) | |
| C02F 1/28 | (2006.01) | |
| C07H 21/02 | (2006.01) | |
| C07H 1/06 | (2006.01) | |

(52) U.S. Cl.
USPC ... 435/287.2; 435/6.1; 435/283.1; 435/288.6; 210/198.2; 210/656; 536/23.1; 536/127

(58) Field of Classification Search
USPC .............. 435/6.1, 283.1, 287.2, 288.5; 210/198.2, 656; 536/23.1, 127
See application file for complete search history.

(56) References Cited

U.S. PATENT DOCUMENTS

| | | | |
|---|---|---|---|
| 5,234,809 A | | 8/1993 | Boom et al. |
| 6,383,393 B1 | | 5/2002 | Colpan et al. |
| 6,426,126 B1 | * | 7/2002 | Conover et al. ............ 427/488 |
| 7,183,002 B2 | | 2/2007 | Sauer et al. |
| 7,208,271 B2 | | 4/2007 | Bost et al. |
| 2004/0091411 A1 | * | 5/2004 | Modrek-Najafabadi ...... 423/338 |
| 2005/0089850 A1 | * | 4/2005 | Van Ness et al. ............... 435/6 |
| 2006/0216816 A1 | * | 9/2006 | Ohnishi .................... 435/287.2 |
| 2007/0084774 A1 | * | 4/2007 | Broske et al. ............ 210/198.2 |
| 2007/0090034 A1 | * | 4/2007 | Ricker et al. ............ 210/198.2 |
| 2007/0267336 A1 | * | 11/2007 | Ohnishi et al. ............ 210/198.2 |

FOREIGN PATENT DOCUMENTS

| | | |
|---|---|---|
| EP | 1 607 748 | 12/2005 |
| JP | 08-501321 | 2/1996 |
| JP | 2002-209580 | 7/2002 |
| JP | 2003-528455 | 9/2003 |
| JP | 2005-110503 | 4/2005 |
| JP | 2005-510233 | 4/2005 |
| JP | 2005-333936 | 12/2005 |
| JP | 2007-068534 | 3/2007 |
| WO | 95/01359 | 1/1995 |
| WO | 03/046146 | 6/2003 |
| WO | 2004/086055 | 10/2004 |

OTHER PUBLICATIONS

Apllied Biosystems brochure—POROS R21, printed Dec. 23, 2010, pp. 1-8.*
Ohnishi, Development of a microcapillary column for detecting targeted messenger RNA molecules, 2006, Journal of Chromatography A, 1109, 122-126, Published online on Dec. 1, 2005.*
Boom et al., "Rapid and Simple Method for Purification of Nucleic Acids," Journal of Clinical Microbiology, Mar. 1990, pp. 495-503.
Tian et al., "Large-pore mesoporous SBA-15 silica particles with submicrometer size as stationary phases for high-speed CEC separation", Electrophoresis, 2006, vol. 27, pp. 742-748.
European Office Action issued Jul. 31, 2012 for corresponding European Appln. No. 07016929.7.

* cited by examiner

Primary Examiner — Narayan Bhat
(74) Attorney, Agent, or Firm — K&L Gates LLP

(57) ABSTRACT

A micro channel for recovering nucleic acid from a biological sample treated with a chaotropic ion, include an integrated portion composed of silica micro beads having a pore size of from 6 to 29 nm is formed in the channel.

9 Claims, 5 Drawing Sheets

CAPILLARY MATERIAL: FUSED SILICA FOR ϕ0.32, PEEK (POLYETHER ETHER KETONE) FOR ϕ0.5 AND 0.75, STAINLESS STEEL FOR ϕ1.0 AND 4.0

MICRO CHANNEL, DEVICE FOR RECOVERING NUCLEIC ACID AND METHOD FOR RECOVERING NUCLEIC ACID

CROSS REFERENCES TO RELATED APPLICATIONS

The present application claims priority to Japanese Patent Application JP 2006-257791 filed in the Japanese Patent Office on Sep. 22, 2006, the entire contents of which are being incorporated herein by reference.

BACKGROUND

The present application relates to a micro channel, a device for recovering nucleic acid and a method for recovering nucleic acid. In more detail, the application relates to a micro channel in which an integrated portion composed of silica micro beads having a pore size of from 6 to 29 nm is formed in the micro channel, a device for recovering nucleic acid having the micro channel and a method for recovering nucleic acid by using the micro channel.

With the development of genome analysis in recent years and the like, there has been made an attempt to introduce genetic testing into the medical site. The genetic testing means testing and analysis to be carried out regarding nucleic acid obtained by, for example, collection from a biological sample. There is a possibility that hereditary diseases and incidence risks thereof, infectious diseases (pathogenic microbes), malignant tumors, and the like can be detected with high accuracy by the genetic testing.

For example, in the case where the genetic testing is carried out by collecting blood or a tissue from a human body or the like, it is required to recover and extract only nucleic acid from a biological sample such as blood.

As a method for recovering and extracting nucleic acid, for example, a BOOM method is known. The BOOM method is a technology for extracting nucleic acid by combining a chaotropic reagent with silica, etc. and utilizes the adsorption of nucleic acid on a silica surface in the presence of a chaotropic ion.

As the related art, for example, JP-A-2005-110503 describes a purification method of nucleic acid by adsorbing nucleic acid on silica; and JP-A-2002-209580 describes a separation method of nucleic acid by adsorbing nucleic acid on glass beads.

In the related-art recovery and extraction method of nucleic acid, silica or the like was adhered to a glass fiber or a membrane (film-like material). For that reason, there was a problem that a lot of voids are present among silica particles, whereby the recovery efficiency of nucleic acid is low. Then, it is desirable to enhance the recovery efficiency of nucleic acid.

SUMMARY

According to an embodiment, there is provided a micro channel for recovering nucleic acid from a biological sample treated with a chaotropic ion, including an integrated portion composed of silica micro beads having a pore size of from 6 to 29 nm is formed in the channel.

By treating a nucleic acid-containing solution (for example, a biological sample) with a chaotropic ion solution and then passing the nucleic acid solution through the micro channel from an upstream side to a downstream side and adsorbing it on the silica micro beads, the nucleic acid can be efficiently recovered.

In addition, for example, by using silica micro beads having an average particle size of not more than 10 μm and having a specific surface area of 320 m2/g or more in the case of a particle size of 5 μm, the recovery amount per se of nucleic acid can be increased, and therefore, the recovery efficiency of nucleic acid can be more enhanced.

The foregoing method can be applied to, for example, a PCR (polymerase chain reaction) device equipped with a channel for feeding nucleic acid and a device for recovering nucleic acid having a channel for feeding nucleic acid into a DNA chip or the like.

According to an embodiment of the application, the recovery efficiency of nucleic acid can be enhanced.

Additional features and advantages are described herein, and will be apparent from, the following Detailed Description and the figures.

DETAILED DESCRIPTION

Figure 1:
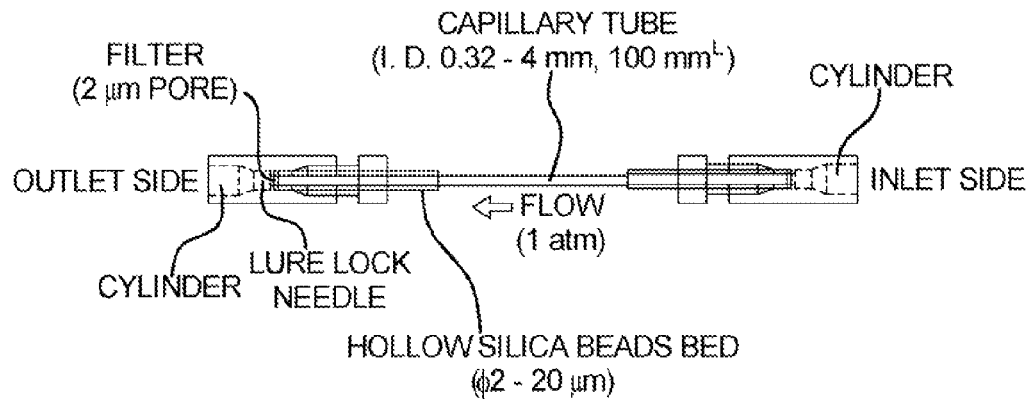
FIG. 1 is a schematic view to show a channel system which is used in an experiment in Example 1.

An example of a micro channel according to an embodiment is described below.

The micro channel may be formed by using a micro tube of, for example, fused silica, a plastic or a metal and may be formed by subjecting a substrate surface of silicon, etc. to etching or the like.

A configuration in which platinum or the like is vapor deposited in a prescribed place in a micro channel, thereby making it possible to apply an electric field in the channel is also employable. For example, in the case of recovering nucleic acid from a biological sample, the sample contains other charge substances such as proteins. For that reason, there is a possibility that such substances are adsorbed on a silica surface. In response to this, for example, by applying an electric field in the channel in the presence of a chaotropic ion, it is possible to liberate the proteins and the like from silica in a state that nucleic acid is adsorbed on the silica surface. Accordingly, the accuracy of extraction of nucleic acid can be enhanced.

An inner diameter in an integrated portion of the micro channel is suitably from 0.32 to 1.00 mm.

This micro channel at least has an integrated portion composed of silica micro beads having a pore size of from 6 to 29 nm in the channel.

As the silica micro beads, any micro beads containing a porous silica particle are useful. The silica particle includes, in addition to a crystal of silicon dioxide, all of silicon oxides in other forms, silica modified with a substituent which is bindable with nucleic acid, and silica containing other composition such as alumina and titanium.

It is preferable that the average particle size of the silica micro beads is not more than 10 μm. By using micro beads having an average particle size of not more than 10 μm, the amount of the micro beads which can be filled in a fine particle can be increased; and also, since the surface area increases, the recovery efficiency of nucleic acid can be enhanced. However, when the average particle size of the silica micro beads is too small, the passing speed of the solution becomes slow, and clogging is easy to occur.

The pore size of the silica micro beads is suitably in the range of from 6 to 29 nm. By using the silica micro beads having a pore size falling within this range, the recovery efficiency of nucleic acid can be more enhanced.

The "pore size" as referred to herein means a diameter (average value) of fine voids which are present on the particle surface of the silica micro bead. The pore size can be measured by a known method, for example, a gas adsorption method (for example, a nitrogen adsorption method), an X-ray diffraction method, and an X-ray small-angle scattering method.

With respect to the silica micro beads, it is more suitable that the specific surface area (surface area in the case of reducing into a prescribed size) is large. When the specific surface area is large, since the recovery amount of nucleic acid increases, the recovery efficiency of nucleic acid can be more enhanced.

Various commercial products are available with respect to the silica micro beads having such characteristics. As the silica micro beads, for example, a silica based mesoporous material may also be used. The mesoporous material can be synthesized by a known method or the like. Examples of the known method include a method of synthesis by hydrolyzing an alkoxide of silicon in the presence of a surfactant; and a method of synthesis by inserting an alkylammonium between layers of phyllosilicate.

An example of a method for recovering nucleic acid according to an embodiment is described below.

For example, the method for recovering nucleic acid according to an embodiment includes at least a procedure of passing a nucleic acid solution treated with a chaotropic ion through the foregoing micro channel to adsorb nucleic acid on the silica micro beads.

As the nucleic acid solution, any solution containing nucleic acid is useful. In the case of a cell-containing biological sample such as blood, for example, a cell lysis solution prepared by dissolving a cell membrane is used as the nucleic acid solution. On that occasion, impurities may be removed by using a filter or the like as a pretreatment.

In the case where nucleic acid is present in a solution containing chaotropic ion, the nucleic acid is adsorbed on the silica micro beads. For that reason, it is necessary to inject the nucleic acid solution treated with a chaotropic ion into the micro channel in advance. Examples of chaotropic substances include guanidine salts (for example, guanidine thiocyanate and guanidine hydrochloride), potassium iodide, sodium iodide, and salts of SCN—.

As a liquid feed method for introducing a nucleic acid solution and other various reagents into the micro channel and passing them through an integrated portion of the silica micro beads, known methods can be employed, and there are no particular limitations. For example, the solution and the like may be sucked or extruded by using a micro pump, etc., or a centrifugal force or the like may be employed.

As a method for eluting and recovering the nucleic acid adsorbed on the silica micro beads, known methods can be employed, and there are no particular limitations. In this method for recovering nucleic acid, in order to achieve the treatment with a chaotropic ion, the nucleic acid can be liberated and eluted by flowing a chaotropic ion-free solution (for example, pure water and a prescribed buffer). On that occasion, for example, the nucleic acid may be recovered by applying an electric field and moving the liberated and eluted nucleic acid into a positive electrode side by force.

Example 1

In Example 1, in the case of forming an integrated portion of silica micro beads in a micro channel, passing a nucleic acid solution through the channel and recovering nucleic acid, the correlation between a bore of the micro channel and the recovery efficiency of nucleic acid was reviewed. The outline of experimental procedures is as follows.

First of all, a channel system (see FIG. 1) to be used for the experiment was assembled. Five kinds of tubes having a different bore were first prepared. The prepared tubes are five kinds including a fused silica tube having a bore of 0.32 mm, a PEEK (polyether ether ketone; hereinafter the same) tube having a bore of 0.5 mm, a PEEK tuber having a bore of 0.75 mm, a stainless steel tube having a bore of 1.0 mm and a stainless steel tube having a bore of 4.0 mm. Lengths of the tubes were all fixed at 10 cm. Next, a cylinder was connected to an upstream side of the tube (right side in FIG. 1) via a connecting part. Also, a lure lock needle was connected to a downstream side of the column (left side in FIG. 1) via a connecting part, and a cylinder was installed in the lure lock needle. A filter having a pore size of 2 μm was set up on the lure lock needle side of the tube.

Subsequently, an integrated portion of silica micro beads was formed in the tube. First of all, hollow silica micro beads (particle size: 2 to 20 μm, manufactured by Polysciences, Inc.) were dispersed in pure water, and the dispersion was charged in the cylinder on the upstream side. Next, the cylinder on the upstream side was pushed while drawing the cylinder on the downstream side, thereby injecting the dispersion into the tube. The injected hollow silica micro beads are dammed up by the filter on the lure lock needle side. Then, the cylinder on the upstream side was pushed while drawing the cylinder on the downstream side, thereby removing water and integrating the hollow silica micro beads on the downstream side in the tube. A length of the integrated portion was controlled by adjusting the amount of the dispersion to be injected.

Subsequently, a nucleic acid solution was injected into this channel system. The preparation of the nucleic acid solution was performed in conformity with a protocol of RNeasy Protect Mini Kit (manufactured by QIAGEN; hereinafter referred to as "kit"). First of all, synthetic single strand DNA (poly A) composed of 120-mer deoxyadenosine was dissolved in RNase-free water (a reagent in the kit; hereinafter the same) to prepare 5 μg/29 μL of a poly A solution. Next, 100 μL of Buffer RLT (a guanidine salt-containing chaotropic ion reagent as a reagent in the kit; hereinafter the same) was added and mixed in this solution. Next, 72 μL of 99.5% ethanol (manufactured by Wako Pure Chemical Industries, Ltd.) was added and mixed in the resulting solution. Next, the prepared nucleic acid solution was injected into the tube by using the cylinders on the upstream side and the downstream side in the same manner as described above.

Subsequently, after rinsing the inside of the tube, the nucleic acid captured by the hollow silica micro beads was recovered. First of all, 280 μL of Buffer RPE (a reagent in the kit; hereinafter the same) in the kit was injected into the tube in the same manner as described above, thereby rinsing the inside of the tube. Substances other than the nucleic acid captured by the hollow silica micro beads were removed by this procedure. Next, 50 μL of RNase-free water was injected into the tube in the same manner as described above, and after passing it through this channel system, the passed solution was recovered. The nucleic acid captured by the hollow silica micro beads was eluted into the solution by this procedure.

Then, the recovered nucleic acid solution was quantitatively determined by using a spectrophotometer (260 nm). The obtained results are shown in FIGS. 2 and 3.

Figure 2:
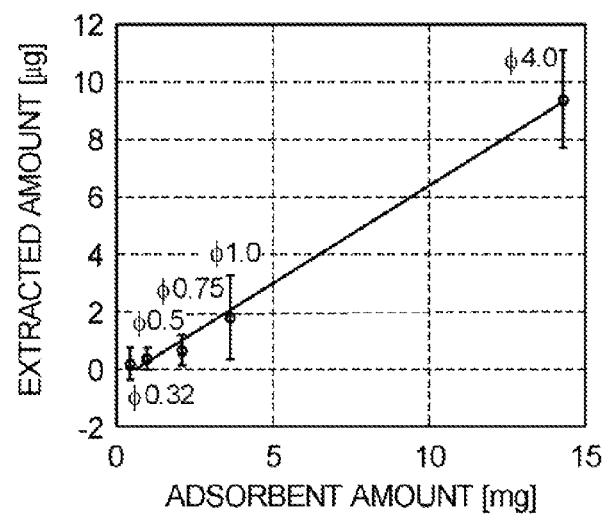
FIG. 2 is a graph to show the correlation between the amount of hollow silica micro beads and the recovery amount of nucleic acid (results of quantitative determination).
Figure 3:
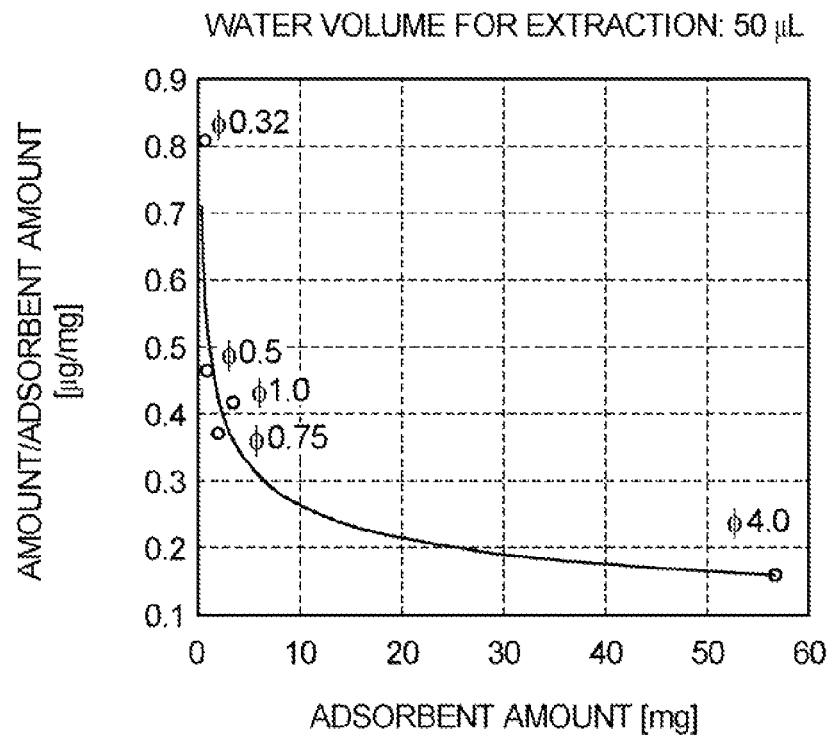
FIG. 3 is a graph to show the recovery efficiency of nucleic acid in Example 1.

FIG. 2 is a graph to show the correlation between the amount of hollow silica micro beads and the recovery amount of nucleic acid (results of quantitative determination); and FIG. 3 is a graph to show the recovery efficiency of nucleic acid. In FIG. 2, the abscissa (Adsorbent amount) represents the amount of micro beads; the ordinate (Extracted amount) represents the amount of recovered nucleic acid (results of quantitative determination); and the respective plots in FIG. 2 represent results at every bore of the tube. In FIG. 3, the abscissa (Adsorbent amount) represents the amount of micro beads similar to FIG. 2; the ordinate (Amount/Adsorbent amount) represents the amount of recovered nucleic acid per mg of micro beads (recovery efficiency of nucleic acid); and the respective plots in FIG. 3 represent results at every bore of the tube. Both of FIGS. 2 and 3 are concerned with the results per 50 μL of the recovered nucleic acid solution.

In FIG. 2, the amount of the used micro beads and the amount of the recovered nucleic acid were substantially proportional to each other. The larger the bore of the tube, the higher the amount of the micro beads which can be filled, and therefore, the amount of the recovered nucleic acid also increased in proportion thereto. On the other hand, in FIG. 3, the smaller the bore of the tube, the higher the recovery efficiency of nucleic acid was.

The foregoing results reveal that the smaller the inside diameter of the channel, the larger the recovery amount of nucleic acid per micro bead and the higher the recovery efficiency of nucleic acid. A suitable inside diameter of the channel as demonstrated by the results of the present experiment is from 0.32 to 1.00 mm.

Reasons why the recovery amount of nucleic acid increases by making the inside diameter of the micro channel small are assumed as follows. That is, when the inside diameter of the micro channel is small, the area of the inner wall surface of the channel decreases, and therefore, the number of nucleic acid molecules passing through the vicinity of the inner wall surface decreases. For that reason, the nucleic acid is easily captured by the silica particle, and the recovery amount of nucleic acid increases. Also, when the inside diameter of the micro channel is small, a portion where the flow amount and the flow rate are non-uniform is hardly generated, and therefore, the adsorption between the nucleic acid molecule and the silica particle is uniformly achieved. For that reason, the recovery amount of nucleic acid increases. In addition, by making the inside diameter of the micro channel small, a gradient in a cross-sectional direction of the channel can be reduced, and therefore, the adsorption between the nucleic acid molecule and the silica particle is uniformly achieved, whereby the recovery amount of nucleic acid increases.

Example 2

In Example 2, in the case of forming an integrated portion of silica micro beads in a micro channel, passing a nucleic acid solution through the channel and recovering nucleic acid, the correlation between a particle size of the silica micro beads and the recovery efficiency of nucleic acid was reviewed.

The outline of experimental procedures is the same as in Example 1. In the present experiment, two kinds of hollow silica micro beads having a different particle size were used. The used hollow silica micro beads are two kinds including micro beads having an average particle size of 10 μm (particle size: 2 to 20 μm) and micro beads having an average particle size of 60 μm (particle size: 15 to 135 μm). The respective micro beads were filled in an amount of 86 μg in the tube. A PEEK tube having a bore of 0.75 mm and a length of 10 cm was used as the tube.

As a result, in the case of using micro beads having an average particle size of 10 μm, about 1 μg of nucleic acid could be recovered. On the other hand, in the case of using micro beads having an average particle size of 60 μm, the nucleic acid could not be substantially recovered. Accordingly, the results of the present experiment reveal that in the case of forming an integrated portion of silica micro beads in the micro channel and recovering nucleic acid, it is better that the particle size of the micro beads is small. A suitable average particle size of the micro beads as demonstrated by the results of the present experiment is not more than 10 μm.

Example 3

In Example 3, the recovery efficiency of nucleic acid in the case of filling silica micro beads in a micro channel and recovering nucleic acid was compared with the recovery efficiency of nucleic acid in the case of adhering silica to a membrane (film-like material) and recovering nucleic acid.

Experimental procedures in the case of filling silica micro beads in a micro channel and recovering nucleic acid were the same as in Example 1 and so on. First of all, an integrated portion of hollow silica micro beads (average particle size: 10 μm) was formed in a tube having an inside diameter of 1 mm. Next, a nucleic acid solution was injected into the tube by using a cylinder; nucleic acid was captured by the silica micro beads; and RNase-free water was then injected into the tube, thereby eluting the nucleic acid into the solution.

On the other hand, experimental procedures in the case of adhering silica to a film-like material (membrane) and recovering nucleic acid were taken in conformity with the foregoing protocol of RNeasy Protect Mini Kit. First of all, a nucleic acid solution was filled in a centrifugal column (RNeasy Minispin Column; hereinafter the same) attached to the kit. Next, the nucleic acid solution was passed through a silica gel membrane in the centrifugal column by a centrifugation treatment, thereby capturing the nucleic acid by the membrane. Next, impurities were rinsed, and the foregoing RNase-free water was then injected into the column, thereby eluting the nucleic acid into the solution.

The obtained results are shown in Table 1. Table 1 shows both of the results in the case of eluting the nucleic acid by using 50 μL of RNase-free water and the results in the case of eluting the nucleic acid by using 200 µL of RNase-free water. In the table, the "Recovery efficiency of nucleic acid" is a value obtained by dividing the recovery amount of nucleic acid by the amount of used silica.

TABLE 1

|  | Amount of eluate (µL) | [A] Amount of silica (mg) | [B] Recovery amount of nucleic acid (µg) | Recovery efficiency of nucleic acid [B]/[A] (µg/mg) |
|---|---|---|---|---|
| Case of using membrane | 50 | 11.9 | 0.94 | 0.08 |
|  | 200 |  | 3.70 | 0.31 |
| Case of using tube | 50 | 0.89 | 0.22 | 0.22 |
|  | 200 |  | 1.19 | 1.19 |

As shown in the results of Table 1, in the case of adhering silica to a membrane and recovering nucleic acid, the recovery amount of nucleic acid was higher; and in the case of filling hollow silica micro beads in a tube having a bore of 1 mm and recovering nucleic acid, the recovery efficiency of nucleic acid was higher. Accordingly, the results of the present experiment reveal that by filling silica micro beads in a micro channel and recovering nucleic acid, the recovery efficiency of nucleic acid can be enhanced and that the amount of silica to be used can be made small.

Example 4

In Example 4, the recovery amount of nucleic acid in the case of using silica micro beads having a large specific surface area was reviewed. Experimental procedures are as follows.

"Inertsil SIL-150A" (manufactured by GL Sciences Inc.; hereinafter referred to as "Inertsil") was used as silica micro beads having a large specific surface area. In the case where Inertsil has a particle size of 5 µm, its specific surface area is 320 m2/g.

First of all, a channel system the same as in Example 1 and so on was assembled by using a tube having a bore of 0.75 mm, and 0.98 mg of Inertsil was injected into the tube, thereby forming an integrated portion of Inertsil. Next, synthetic single strand DNA (poly A) composed of 120-mer deoxyadenosine was dissolved in RNase-free water; 200 µL of Buffer RLT (a guanidine salt-containing chaotropic ion reagent) was then added; and 70.0% ethanol (manufactured by Wako Pure Chemical Industries, Ltd.) was subsequently added to prepare a nucleic acid solution. Next, the nucleic acid solution was injected into the tube and then rinsed by using Buffer RPE, thereby removing impurities. Next, the nucleic acid was eluted with 200 µL of RNase-free water. Then, the recovered nucleic acid solution was quantitatively determined by means of ultraviolet ray absorption spectroscopy. The case of recovering nucleic acid by the hollow silica micro beads (a specific surface area thereof is assumed to be 0.6 m2/g) as used in Example 1 and so on and the case of recovering nucleic acid by using a centrifugal column attached to the foregoing kit were also quantitatively determined, respectively as a control in the same manner.

Figure 4:
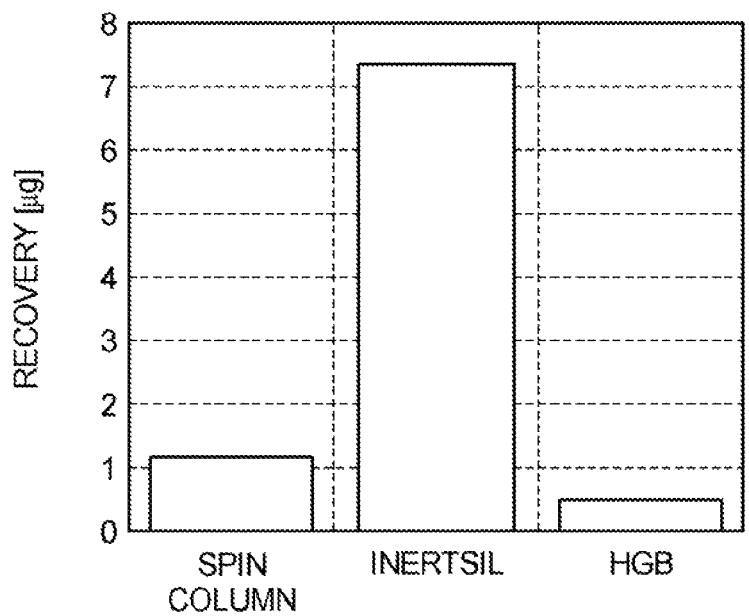
FIG. 4 is a graph to show the recovery amount of nucleic acid in the case of using silica micro beads having a large specific surface area in Example 4.

The obtained results are shown in FIG. 4. In FIG. 4, the ordinate (Recovery) represents the recovery amount of nucleic acid. In FIG. 4, "Spin column" represents the recovery amount of nucleic acid in the case of recovering nucleic acid by using a centrifugal column attached to the foregoing kit; "Inertsil" represents the recovery amount of nucleic acid in the case of using Inertsil as the silica micro beads; and "HGB" represents the recovery amount of nucleic acid in the case of using the hollow silica micro beads, respectively.

As shown in FIG. 4, in the case of using Inertsil, the nucleic acid could be recovered in a ratio of about 10 times of that in the case of using hollow silica micro beads and about 6 times of that in the case of using a centrifugal column, respectively. Accordingly, the results of the present experiment reveal that by using silica micro beads having a large specific surface area, the recovery amount of nucleic acid can be made larger while using the same channel system as in Example 1 and so on.

Example 5

In Example 5, total RNA was actually recovered from live cells by using a micro channel having an integrated portion of silica micro beads formed therein. The outline of experimental procedures is as follows.

First of all, live cells were dissolved, and at the same time, impurities were removed. In the present experiment, HeLa cells were used as the live cells. HeLa cells in a number of cells of from 105 to 106 were first dissolved by using PAXgene (manufactured by QIAGEN) to obtain a cell lysis solution. Next, this cell lysis solution was charged in a column having a spin filter and subjected to a centrifugation treatment to remove impurities (prefiltering). The prefiltering was carried out once or twice.

Subsequently, the cell lysis solution having been subjected to prefiltering was injected into a channel system, thereby adsorbing nucleic acid on silica. As the channel system, the same channel system as in Example 1 and so on was assembled and used. A tube having a bore of 0.75 mm was used as the tube. Inertsil as used in Example 4 was used as the silica micro beads. In the present experiment, two kinds of tubes including a tube having 0.5 mg of Inertsil filled therein and a tube having 1.0 mg of Inertsil filled therein were prepared. After adding 50 µL of ethanol in the cell lysis solution having been subjected to prefiltering, the resulting solution was injected into the foregoing channel system. Then, the cell lysis solution was passed through an integrated portion of Inertsil, thereby adsorbing the nucleic acid contained in the live cells on Inertsil.

Subsequently, after rinsing silica, the nucleic acid adsorbed on silica was eluted and quantitatively determined. First of all, 700 µL of Buffer RW1 (a reagent in the foregoing kit, manufactured by QIAGEN) and 2 mL of Buffer RPE were successively passed through the tube, thereby rinsing the inside of the channel system. Next, 200 µL of RNase-free water was passed therethrough, and the nucleic acid captured by Inertsil was eluted into the solution. Then, the recovered nucleic acid solution was quantitatively determined by means of ultraviolet ray absorption spectroscopy.

As a control, nucleic acid was recovered from a cell lysis solution having been subjected to prefiltering by using a centrifugal column attached to the foregoing kit and quantitatively determined in the same manner as described above.

Figure 5:
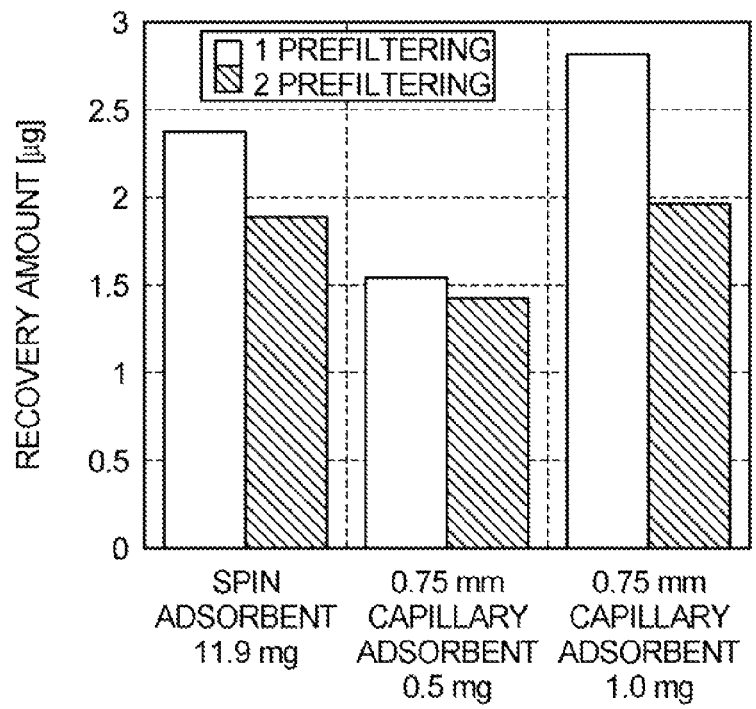
FIG. 5 is a graph to show the recovery amount of nucleic acid extracted from HeLa cells in Example 5.

The obtained results are shown in FIG. 5. In FIG. 5, the ordinate (Recovery) represents the recovery amount of nucleic acid. In FIG. 5, "Spin Adsorbent" represents the recovery amount of nucleic acid in the case of recovering nucleic acid by using a centrifugal column attached to the foregoing kit; "0.75 mm capillary Adsorbent 0.5 mg" represents the recovery amount of nucleic acid in the case of filling 0.5 mg of Inertsil in a tube having a bore of 0.75 mm; and "0.75 mm capillary Adsorbent 1.0 mg" represents the recovery amount of nucleic acid in the case of filling 1.0 mg of Inertsil in a tube having a bore of 0.75 mm, respectively. In FIG. 5, "1 Prefiltering" represents the recovery amount of nucleic acid in the case of performing the prefiltering of the cell lysis solution once; and "2 Prefiltering" represents the recovery amount of nucleic acid in the case of performing the prefiltering of the cell lysis solution twice, respectively.

The results of FIG. 5 reveal that even in the case of filling silica in a micro channel and recovering nucleic acid, by using silica micro beads having a large specific surface area, the recovery amount of nucleic acid can be increased to an extent substantially the same as in the case of adhering silica to a membrane and recovering nucleic acid. That is, the results of the present experiment reveal that in the case of actually recovering nucleic acid from a biological sample, by filling silica micro beads having a large specific surface area in a micro channel, not only the recovery amount of nucleic acid can be increased to an extent substantially the same as in a related-art method, but the recovery efficiency of nucleic acid can be enhanced as compared with that in a related-art method.

Example 6

In Example 6, a micro channel system was assembled by using silica micro beads having a small pore size, and total RNA was recovered by live cells by using this micro channel system. The outline of experimental procedures is as follows.

First of all, a channel system substantially the same as in Example 1 was assembled. A PEEK tube having a bore of 0.75 mm, an outer diameter of 1/16 inches and a length of 10 cm was prepared, and an internal union having a pore size of 2 μm was installed in both ends of the tube by using a nut and a ferrule. On that occasion, a filter having a pore size of 2 μm was installed in a tip of one side of the tube. A lure lock needle was connected to the internal union on the side on which the filter was installed, and a fill port was connected to the internal union on the opposite side thereto.

Subsequently, silica micro beads were filled in the tube. Four kinds of silica micro beads having an average particle size of 10 μm and a pore size of 5 nm, 10 nm, 12 nm and 30 nm, respectively were prepared as an adsorbent (see Table 2). A lure lock type cylinder and a cylinder for RHEODYNE ("RHEODYNE" is a company name and a registered trademark; hereinafter the same) were installed on the side of the lure lock needle and the side of the fill port of the assembled channel system, respectively; and by charging a silica liquid in the cylinder for RHEODYNE and drawing a piston of the lure lock cylinder, the silica liquid was filled in the tube. Also, by supplying air by using the cylinder, water (liquid layer) remaining in the tube was removed. According to these procedures, the silica micro beads were dammed up by the filter part, and an integrated portion of the silica micro beads was formed in the tube.

TABLE 2

| Average particle size (μm) | Pore size (nm) | Specific surface area (m²/g) | Filling amount (mg) | Surface area (m²) |
|---|---|---|---|---|
| 10 | 5 | 450 | 1.053 | 0.47385 |
| 10 | 10 | 350 | 1.027 | 0.35945 |
| 10 | 12 | 200 | 1.015 | 0.203 |
| 10 | 30 | 100 | 1.011 | 0.1011 |

Subsequently, a sample was prepared. For the preparation of a sample, the foregoing RNeasy Protect Mini Kit (manufactured by QIAGEN) was used. HeLa cells were cultivated; the cells were dissolved by using Buffer RLT in the kit; and thereafter, a nucleic acid solution was obtained in conformity with the protocol. Then, this nucleic acid solution was charged in a column having a spin filter and subjected to a centrifugation treatment, thereby removing impurities (prefiltering). Here, the prefiltering was performed three times in total, and three kinds of centrifugal columns ("Amicon Ultrafree-MC", a centrifugal filter column manufactured by Millipore Corporation) having a pore size of 5 μm, 0.45 μm and 0.1 μm, respectively were used in the order from one having a large pore size.

Subsequently, the nucleic acid solution was injected into this channel system. In the assembled channel system, the fill port was taken away on the opposite side to the side on which the filter was installed, and instead of that, another tube was installed. An internal union was installed in the other end of that tube by using a nut and a ferrule such that a liquid phase could be injected into the channel system; a lure lock needle was connected thereto; and a lure lock type cylinder was installed therein. Then, the filter side was evacuated, and the sample was injected into the channel system (the inside of the tube) from the lure lock type cylinder on the opposite side thereto by using a micro cylinder pump, thereby adsorbing nucleic acid on silica.

Subsequently, the nucleic acid (total RNA) as captured by the silica micro beads in the channel system was recovered. 700 μL of Buffer RW1 (a reagent in the kit) and 5 mL of Buffer RPE (a reagent in the kit) were injected into the channel system, thereby rinsing the inside of the channel system. Substances other than nucleic acid as captured by the silica micro beads were removed by this procedure. Next, 100 μL of RNase-free water was injected into the channel system, and the passed solution was recovered. The nucleic acid captured by the silica micro beads was eluted into the solution by this procedure.

Then, the recovered nucleic acid solution was quantitatively determined by using a spectrophotometer (260 nm).

Figure 6:
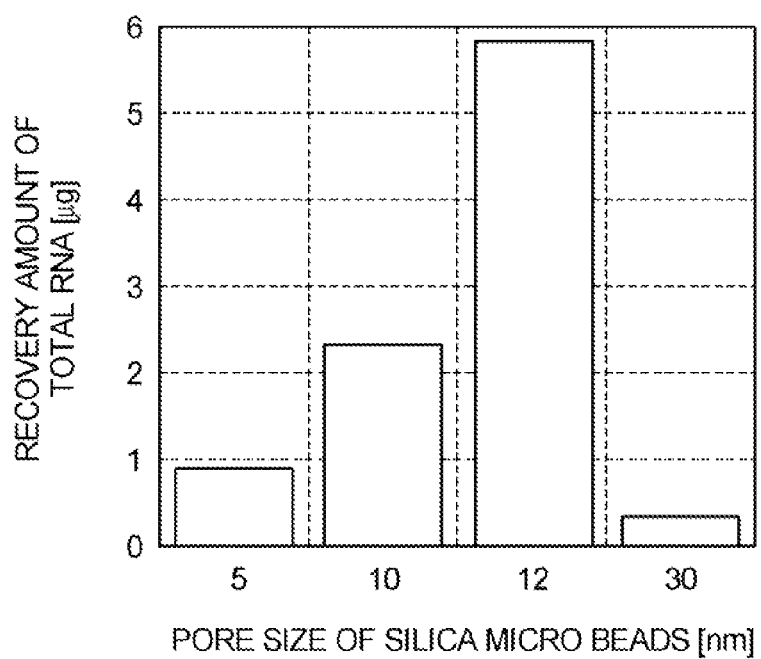
FIG. 6 is a graph to show the recovery amount of total RNA at every pore size of silica micro beads in Example 6.
Figure 7:
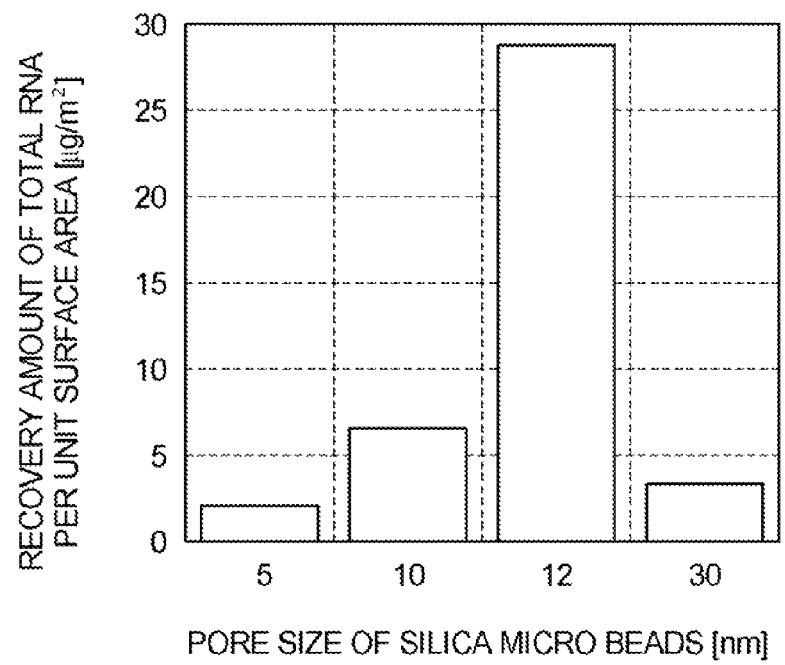
FIG. 7 is a graph to show the recovery amount of total RNA per unit specific surface at every pore size of silica micro beads in Example 6.

The obtained results are shown in FIGS. 6 and 7. FIG. 6 is a graph to show the recovery amount of total RNA at every pore size of silica micro beads; and FIG. 7 is a graph to show the recovery amount of total RNA per unit specific surface area at every pore size of silica micro beads. In both of FIGS. 6 and 7, the abscissa in each graph represents the pore size of silica micro beads (unit: nm). The ordinate in the graph of FIG. 6 represents the recovery amount of total RNA (unit: μg); and the ordinate in the graph of FIG. 7 represents a value obtained by dividing the recovery amount of total RNA by the unit surface area (unit: μg/m2), respectively.

Since the nucleic acid is adsorbed on the surfaces of silica micro beads due to an effect of a chaotropic ion and recovered due to desorption thereof, it can be assumed that the recovery amount of nucleic acid is correlated with a specific surface area (surface area per unit weight) of the silica micro bead. On the other hand, as shown in Table 2, the filling amount of the respective silica micro beads is substantially equal to each other. Accordingly, it can be assumed that the recovery amount of nucleic acid is correlated with the unit surface area of silica micro beads.

On the other hand, according to the results of FIG. 7, with respect to the recovery amount of total RNA per unit surface area, in the case where the pore size of silica micro beads is 5 nm or 30 nm, the recovery amount and the unit surface area were substantially correlated with each other; whereas in the case where the pore size of silica micro beads is 10 nm, the recovery amount per unit surface area was high, and furthermore, in the case where the pore size of silica micro beads is 12 nm, the recovery amount per unit surface area was remarkably high.

These results suggest that in the case where the pore size is 10 nm or 12 nm, especially in the case where the pore size is 12 nm, the adsorption amount of nucleic acid on the silica micro beads remarkably increases. That is, the results of the present experiment suggest that by using silica micro beads having a pore size in the vicinity of 12 nm (for example, from 6 to 29 nm, and more suitably from 11 to 29 nm), it is possible to increase remarkably the recovery amount of nucleic acid.

Example 7

In Example 7, after performing prefiltering of a sample by using a filter having a pore size of 10 μm, total RNA was recovered. The outline of experimental procedures is as follows.

First of all, a sample was prepared. For the preparation of a sample, a reagent attached to the foregoing RNeasy Protect Mini Kit (manufactured by QIAGEN) was used. HeLa cells were cultivated; the cells were dissolved by using Buffer RLT in the kit; and thereafter, a cell lysis solution was obtained in conformity with the protocol.

Subsequently, prefiltering of the cell lysis solution was performed. The cell lysis solution was charged in a spin column equipped with a centrifugal filter having a pore size of 10 μm ("MicroSpin Empty Columns", manufactured by GE Healthcare Bioscience) and centrifuged to remove impurities. Furthermore, impurities were removed by using a spin column equipped with a centrifugal filter having a pore size of 5 μm ("Amicon Ultrafree-MC", manufactured by Millipore Corporation).

Then, total RNA was recovered by using the foregoing kit, and the recovered total RNA was quantitatively determined by using a spectrophotometer (260 nm).

Figure 8:
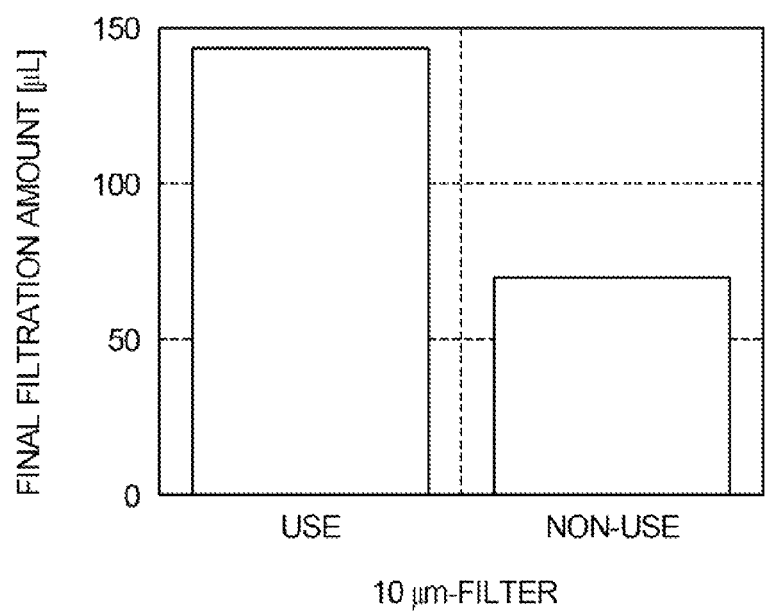
FIG. 8 is a graph to show the final filtration amount after completion of the treatment of all filters in the case of performing a filtering treatment by a spin column equipped with a centrifugal filter having a pore size of 10 μm in Example 7.
Figure 9:
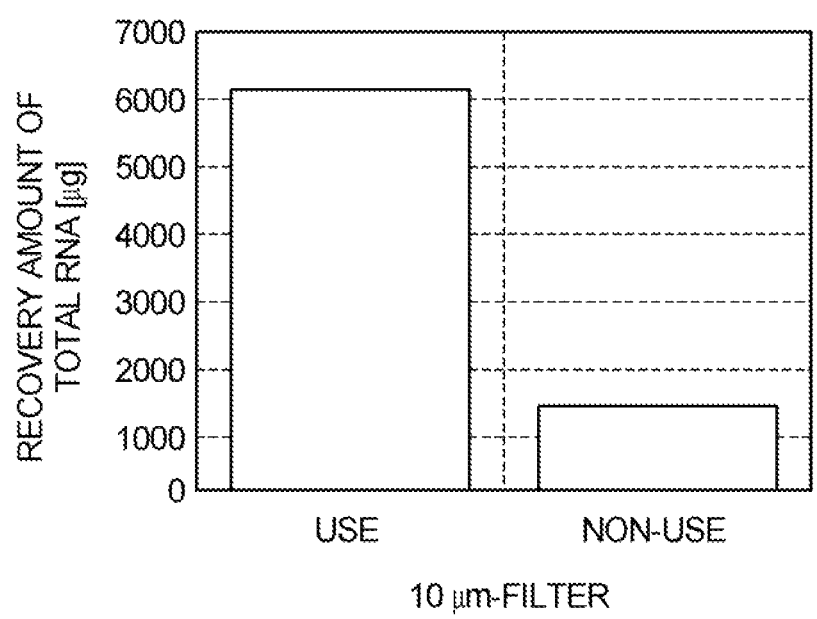
FIG. 9 is a graph to show the recovery amount of total RNA in the case of performing a filtering treatment by a spin column equipped with a centrifugal filter having a pore size of 10 μm in Example 7.

The obtained results are shown in FIGS. 8 and 9. FIG. 8 is a graph to show the final filtration amount after completion of the treatment of all filters in the case of performing a filtering treatment by a spin column equipped with a centrifugal filter having a pore size of 10 μm; and FIG. 9 is a graph to show the recovery amount of total RNA similarly. In both of FIGS. 8 and 9, the abscissa in each graph represents the presence or absence of the use of a centrifugal filter having a pore size of 10 μm. The ordinate in the graph of FIG. 8 represents the final filtration amount (unit: μL); and the ordinate in the graph of FIG. 9 represents the recovery amount of total RNA (unit: ng), respectively.

As shown in FIG. 8, in the case where the prefiltering is performed by using a centrifugal filter having a pore size of 10 μm, the final filtration amount after completion of the treatment of all filters remarkably increased as compared with the case where a centrifugal filter having a pore size of 10 μm is not used. Also, in the case where a centrifugal filter having a pore size of 10 μm is not used, clogging of the filter having a pore size of 5 μm was generated. These results reveal that a lot of impurities of 10 μm or more are contained in the cell lysis solution.

Also, as shown in FIG. 9, in the case where the prefiltering is performed by using a centrifugal filter having a pore size of 10 μm, the recovery amount of total RNA remarkably increased as compared with the case of not using a centrifugal filter having a pore size of 10 μm. These results reveal that by performing the prefiltering by using a centrifugal filter having a pore size of 10 μm, clogging on the filter having a pore size of 5 μm can be suppressed, whereby the recovery efficiency of total RNA can be enhanced.

Accordingly, the results of the present experiment suggest that by performing the prefiltering of a sample by using a centrifugal filter having a pore size in the vicinity of 10 μm (for example, a pore size of from 6 μm to 25 μm) or the like, the recovery efficiency of nucleic acid can be increased.

In genetic testing or the like, only nucleic acid is extracted from a biological sample such as blood, the extracted nucleic acid is fed into each reaction region of a DNA chip or the like and analyzed by a device for detecting nucleic acid or the like. By using an embodiment according to the application, for example, in a channel for feeding a biological sample into a DNA chip or the like, it is possible to extract nucleic acid from the biological sample and to feed the extract into the DNA chip. That is, for example, by incorporating an embodiment according to the application into a device for feeding nucleic acid, it is possible to feed nucleic acid extracted from a biological sample more simply and by means of automatic processing into a reaction region of a DNA chip or the like.

A device for feeding nucleic acid per se can also be incorporated into a nucleic acid analyzer. According to this, there is a possibility that a series of operations of from feed of a biological sample to genetic analysis can be automated; and there is a possibility that integration and downsizing of the device can be realized.

An embodiment can also be incorporated into a device capable of achieving PCR (polymerase chain reaction), for example, a PCR device and a sequencer. For example, by passing a biological sample through a micro channel and feeding an extracted nucleic acid solution into a reaction region, a pretreatment such as PCR can be simplified. Also, according to this, it is possible to realize automation of a series of operations or downsizing of the device.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A device for recovering a nucleic acid from a biological sample, comprising: a micro tube having an inner diameter of 0.32 mm to 1.00 mm containing a bed of silica micro beads having a pore size of from 6 to 29 nm configured to adsorb the nucleic acid in the biological sample, which includes a chaotropic ion; a cylinder connected to an inlet side of the micro tube through a second tube; and a filter located at the outlet side of the micro tube.

2. The device according to claim 1, wherein an average particle size of the silica micro beads is not more than 10 μm.

3. The device according to claim 1, wherein the silica micro beads have a specific surface area of 320 $m^2/g$ or more in the case of a particle size of 5 μm.

4. A device according to claim 1, wherein platinum is vapor deposited in a portion of the micro tube.

5. A device according to claim 1, wherein the micro tube further comprises a material selected from the group consisting of: fused silica, plastic or metal.

6. A method for recovering a nucleic acid from a biological sample, comprising the step of: passing the biological sample through the device of claim 1.

7. The method for recovering the nucleic acid from the biological sample according to claim 6, wherein an average particle size of the silica micro beads is not more than 10 μm.

8. The method for recovering the nucleic acid from the biological sample according to claim 6, wherein the silica micro beads have a specific surface area of 320 m$^2$/g or more in the case of a particle size of 5 μm.

9. The method for recovering the nucleic acid from the biological sample according to claim 6, further comprising the step of: performing filtering of a sample as a pretreatment.

\* \* \* \* \*